(12) United States Patent
Kelly et al.

(10) Patent No.: US 6,727,270 B2
(45) Date of Patent: Apr. 27, 2004

(54) PYRROLYLALKYLIDENE-HYDRAZINECARBOXIMIDAMIDE DERIVATIVES AS 5-HYDROXYTRYPTAMINE-6 LIGANDS

(75) Inventors: Michael Gerard Kelly, Thousand Oaks, CA (US); Ping Zhou, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/366,011

(22) Filed: Feb. 13, 2003

(65) Prior Publication Data
US 2003/0203895 A1 Oct. 30, 2003

Related U.S. Application Data

(60) Provisional application No. 60/357,032, filed on Feb. 14, 2002.

(51) Int. Cl.[7] ............ A61K 31/40; A61P 3/04; A61P 25/06; C07D 207/48; C07D 409/12
(52) U.S. Cl. ......... 514/370; 514/415; 514/422; 514/424; 548/164; 548/491; 548/505; 548/527; 548/542
(58) Field of Search .............. 514/370, 415, 514/422, 424; 548/164, 491, 505, 542, 527

(56) References Cited

FOREIGN PATENT DOCUMENTS

| EP | 0505322 B | * | 9/1998 |
| EP | 1057812 A | * | 12/2000 |
| WO | 02059088 A | * | 8/2002 |
| WO | 03068740 | * | 8/2003 |

OTHER PUBLICATIONS

Buchheit, et al, Bioorganic and Medicinal Chemistry Letters, 1995, 5(21), 2495–2500.*

* cited by examiner

*Primary Examiner*—Joseph K. McKane
*Assistant Examiner*—Andrea D. Small
(74) *Attorney, Agent, or Firm*—Barbara L. Lences

(57) ABSTRACT

The present invention provides a compound of formula I and the use thereof for the therapeutic treatment of disorders relating to or affected by the 5-HT6 receptor.

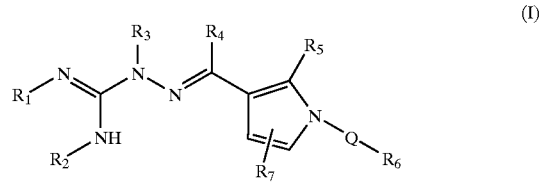

(I)

20 Claims, No Drawings

PYRROLYLALKYLIDENE-HYDRAZINECARBOXIMIDAMIDE DERIVATIVES AS 5-HYDROXYTRYPTAMINE-6 LIGANDS

This application claims priority from co-pending application Ser. No. 60/357,032, filed on Feb. 14, 2002, the entire disclosure of which is hereby incorporated by reference.

BACKGROUND OF THE INVENTION

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1 A), the 5-HT2 family (e.g. 5-HT2A), 5-HT3,5-HT4,5-HT5,5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA are seen in the granular layer of the cerebellum, several diencephalic nuclei, amygdala and in the cortex.

Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia or bulimia), neurodegeherative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a pyrrolylalkylidene-hydrazinecarboximidamide derivative of formula I

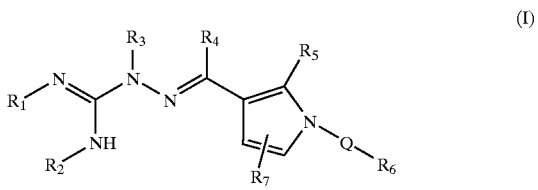

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a 5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S; or the stereoisomers thereof or the pharmaceutically acceptable salts thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D.C. Rogers, Current Opinion in Investigational Drugs, 2001, 2(1):104–109, Pharma Press Ltd.

Surprisingly, it has now been found that pyrrolylalkylidene-hydrazine-carboximidamide derivatives of formula I demonstrate 5-HT6 affinity. Advantageously, said hydrazine derivatives may be used as effective therapeutic agents for the treatment of central nervous system (CNS) disorders associated with or affected by the 5-HT6 receptor. Accordingly, the present invention provides pyrrolylalkylidene-hydrazinecarboximidamide derivatives of formula I

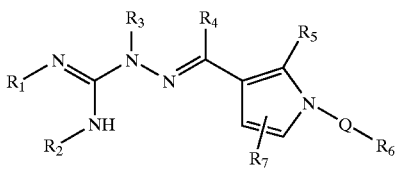

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a 5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S; or the stereoisomers thereof or the pharmaceutically acceptable salts thereof.

As used in the specification and claims, the term halogen designates Br, Cl, I or F and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR, O or S; and R is H or an optional substituent as described hereinbelow:

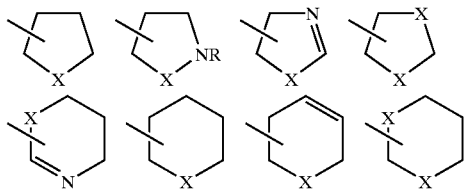

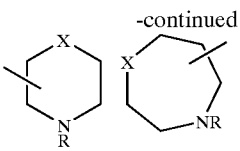

Similarly, as used in the specification and claims, the term heteroaryl designates a $C_5$–$C_{10}$ aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynyl, $C_3$–$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl groups. Typically, 0–3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein Q is $SO_2$. Also preferred are those compounds wherein $R_4$ is H or $CH_3$. Another group of preferred formula I compounds are those compounds wherein $R_6$ is an optionally substituted phenyl or heteroaryl group.

More preferred compounds of the invention are those compounds of formula I wherein Q is $SO_2$ and $R_6$ is an optionally substituted phenyl or heteroaryl group. Another group of more preferred compounds of the invention are those formula I compounds wherein Q is $SO_2$; $R_4$ is H or $CH_3$; $R_5$ is H; and $R_6$ is an optionally substituted phenyl or heteroaryl group. Further more preferred compounds of formula I are those compounds wherein Q is $SO_2$; $R_1$, $R_2$, $R_3$, $R_5$ and $R_7$ are H; $R_4$ is H or $CH_3$; and $R_6$ is an optionally substituted phenyl or heteroaryl group.

Among the preferred compounds of the invention are:

2-{(E)-1-[1-(phenylsulfonyl)-1H-pyrrol-3-yl]ethylidene}hydrazinecarboximidamide;
2-{(E)-1-[1-(4-methylphenylsulfonyl)-1H-pyrrol-3-yl]ethylidene}hydrazine-carboximidamide;
2-{(E)-1-[1-(2,4-dimethyl-1-(phenylsulfonyl)-1H-pyrrol-3-yl]ethylidene}hydrazine-carboximidamide;
2-{(E)-1-[1-(naphthylsulfonyl)-1H-pyrrol-3-yl]ethylidene}-1-hydrazine-carboximidamide;
2-{(E)-1-{1-(5-chloro-3-methyl-1-benzothiophen-2-yl)sulfonyl]-1H-pyrrol-3-yl}ethylidene)-1-hydrazinecarboximidamide;
2-((E)-1-{1-[(4-aminophenyl)sulfonyl]-1H-pyrrol-3-yl}ethylidene)-1-hydrazine-carboximidamide;
2-((E)-1-{1-[(2-amino-4-methyl-1,3-thiazol-5-yl)sulfonyl]-1H-pyrrol-3-yl}ethylidene)-1-hydrazinecarboximidamide;
2-[1-[(phenylsulfonyl)-1,5,6,7-tetrahydro-4H-indol-4-ylidene]-1-hydrazinecarboximidamide;
2-[1-(4-biphenylsulfonyl)-1,5,6,7-tetrahydro-4H-indol-4-ylidene]-1-hydrazinecarboximidamide;
2-[1-(4-bromophenylsulfonyl)-1,5,6,7-tetrahydro-4H-indol-4-ylidene]-1-hydrazinecarboximidamide;
2-[1-(5-chloro-2-methoxyphenylsulfonyl)-1,5,6,7-tetrahydro-4H-indol-4-ylidene]-1-hydrazinecarboximidamide;

the stereoisomers thereof; or the pharmaceutically acceptable salts thereof.

Compounds of the invention may be prepared by using conventional synthetic methods and, if required, standard separation and isolation techniques. For example, compounds of formula I wherein Q is $SO_2$ and $R_5$ is H (Ia) may be prepared by reacting a 3-acylpyrrole compound of formula III with a sulfonyl chloride, $R_6SO_2Cl$, in the presence of a base, such as NaH, to give the corresponding 1-sulfonyl-3-acylpyrrole of formula II and condensing said pyrrole with an aminoguanidine of formula IV to give the desired formula Ia product. The reaction is shown in flow diagram I.

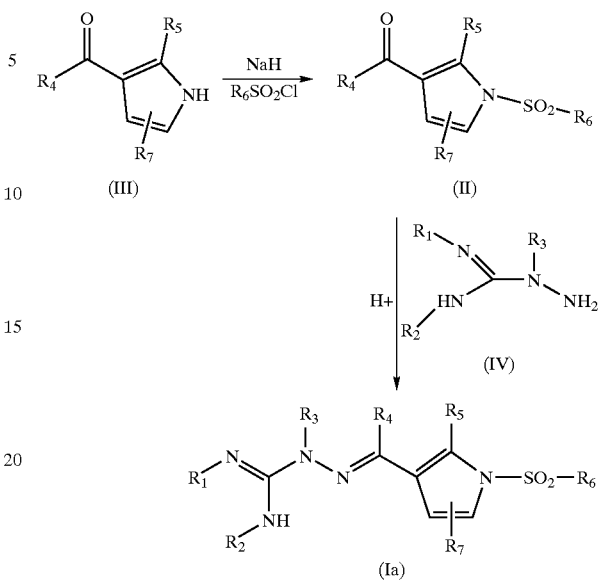

Compounds of formula I wherein Q is $SO_2$ and $R_4$ and $R_5$ are taken together with the atoms to which they are attached to form a 5-, 6- or 7-membered ring (Ib) may be prepared by reacting the appropriate pyrrole derivative of formula V with a sulfonyl chloride, $R_6SO_2Cl$, to form the corresponding N-sulfonyl compound of formula VI and condensing said formula VI compound with an aminoguanidine of formula IV to give the desired product of Formula Ib. The reaction is shown in flow diagram II wherein n is an integer of 1, 2 or 3.

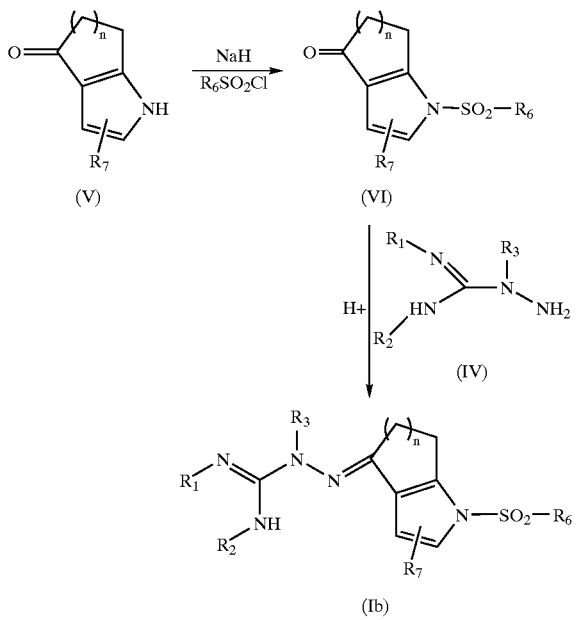

Similarly, compounds of formula I wherein Q is CO, $CH_2$, $CO_2$, CONRR or CSNRR may be prepared using the above procedures illustrated in flow diagram I and II and employing the appropriately substituted acid chloride, alkylhalide, chloroformate, isocyanate or isothiocyanate, respectively, in place of $R_6SO_2Cl$.

Advantageously, the present invention provides a process for the preparation of a compound of formula I which comprises reacting a compound of formula IIa with an aminoguanidine of formula IV in the presence of an acid, optionally in the presence of a solvent. The process of the invention is shown in flow diagram III.

Flow Diagram III

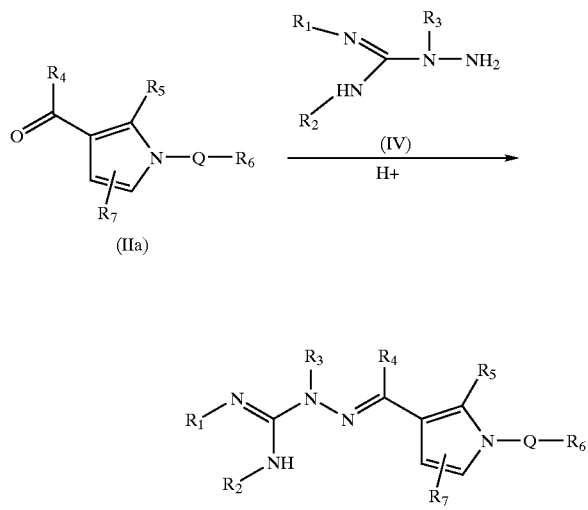

Acids suitable for use in the process of the invention include acids such as HCl, HBr, $H_2SO_4$, $HNO_2$ or the like, preferably HCl. Solvents suitable for use in the process of invention include protic solvents such as lower alkyl alcohols, i.e., methanol, ethanol, isopropanol, propanol or the like, preferably isopropanol.

Advantageously, the inventive compound of formula I may-be utilized in the treatment of central nervous system disorders relating to or affected by the 5-HT6 receptor such as motor, mood, psychiatric, cognitive, neurodegenerative, or the like disorders, for example, Alzheimer's disease, Parkinson's disease, attention deficit disorder, anxiety, epilepsy, depression, obsessive compulsive disorder, migraine, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term NMR designates proton nuclear magnetic resonance. The terms THF and EtOAc designate tetrahydrofuran and ethyl acetate, respectively.

EXAMPLE 1
Preparation of 1-[2,4-Dimethyl-1-phenylsulfonyl)-1H-pyrrol-3-yl]-1-ethanone

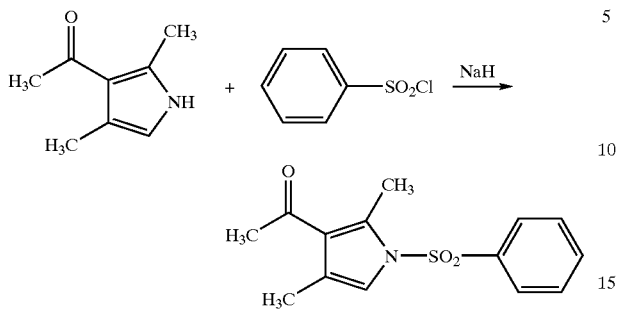

A stirred solution of 3-acetyl-2,4-dimethylpyrrole (1.0 g, 7.3 mmol) in dry THF is treated portionwise with NaH (60% in mineral oil, 0.44 g, 11.0 mmol) under nitrogen at room temperature, stirred for 0.5 hr, treated with benzenesulfonyl chloride (1.1 ml, 8.8 mmol), stirred for 24 hr, quenched with water and diluted with EtOAc. The phases are separated. The organic phase is washed sequentially with water and brine, dried over $MgSO_4$ and concentrated in vacuo. The resultant residue is purified by flash chromatography (silica gel, EtOAc/hexanes, 2/8 as eluent) to afford the title compound as an off-white solid, 1.70 g, (84% yield) mp 110–112° C., identified by NMR and mass spectral analyses.

EXAMPLES 2–5
Preparation of 1-Arylsulfonyl-3-acetylpyrrole

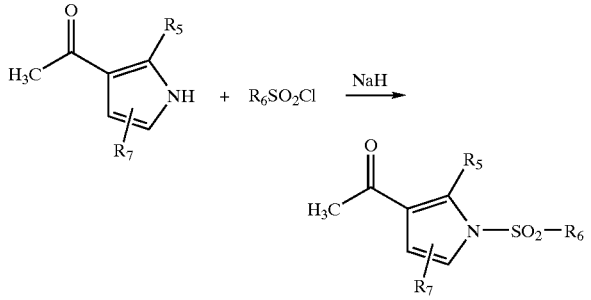

Using essentially the same procedure described in Example 1 and substituting the appropriate 3-acetypyrrole substrate and arylsulfonyl chloride, the compounds shown in Table I are obtained and identified by NMR and mass spectral analyses.

EXAMPLE 6
Preparation of 1-(Phenylsulfonyl)-1,5,6,7-tetrahydro-4H-indol-4-one

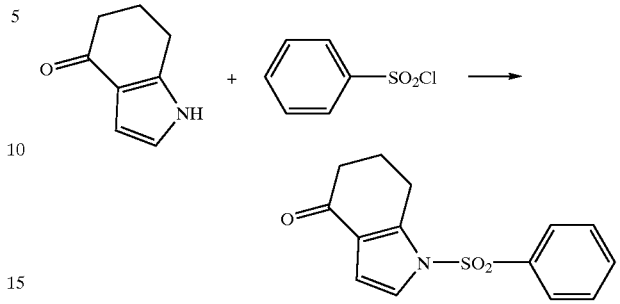

A stirred solution of 1,5,6,7-tetrahydro-4H-indol-4-one (5.0 g, 37.0 mmol) in THF is treated portionwise with NaH (60% dispersion in mineral oil, 1.5 g, 37.0 mmol) under $N_2$ at room temperature, stirred for 0.5 hr, treated with benzene sulfonyl chloride (4.7 ml, 37.0 mmol), stirred for 24 hr, quenched with water and diluted with EtOAc. The phases are separated. The organic phase is washed sequentially with water and brine, dried over $MgSO_4$ and concentrated in vacuo. The resultant residue is purified by flash chromatography (silica gel, EtOAc/hexanes, 1/1 as eluent) to afford the title product as an off-white solid, 8.72 g (85% yield), mp 108–110° C., identified by NMR and mass spectral analyses.

EXAMPLE 7
Preparation of 2-[1-(Phenylsulfonyl)-1,5,6,7-tetrahydro-4H-indol-4-ylidine]-1-hydrazinecarboximidamide Hydrochloride

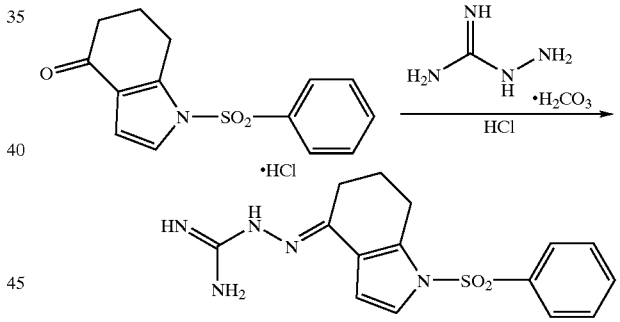

A stirred solution of 1-(phenylsulfonyl)-1,5,6,7-tetrahydro-4H-indol-4-one (275 mg, 1 mmol) in isopropyl

TABLE I

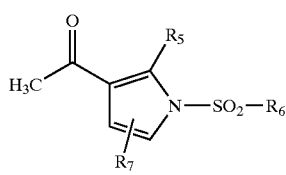

| Ex. No. | R5 | R7 | R6 | mp ° C. | % Yield |
|---|---|---|---|---|---|
| 2 | H | H | 1-naphthyl | 85–87 | 67 |
| 3 | H | H | 5-chloro-3-methylbenzo[b]thien-2-yl | 113–115 | 49 |
| 4 | H | H | 4-acetamidophenyl | 175–176 | 65 |
| 5 | H | H | 2-acetamido-4-methyl-1,3-thiazol-5-yl | 173–175 | 59 | alcohol is treated with aminoguanidine bicarbonate (150 mg, 1.1 mmol) and concentrated HCl (1 ml), heated at 65° C., under $N_2$, for 18 hr, cooled to room temperature and concentrated in vacuo. The resultant residue is dispersed in methylene chloride and water and filtered. The filter cake is air-dried to afford the title product as an off-white solid, 355 mg (97% yield), mp 157–159° C., identified by NMR and mass spectral analyses.

EXAMPLES 8–12

Preparation of 1-Arylsulfonyl-1,5,6,7-tetrahydro-4H-indol-4-ylidene-1-hydrazinecarboximidamide Hydrochloride

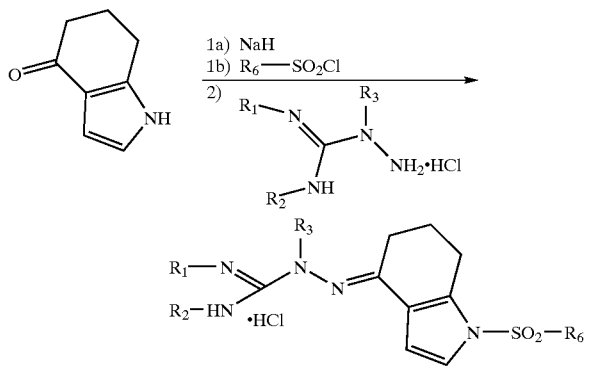

Using essentially the same procedures described in Examples 6 and 7 and employing the appropriate arylsulfonyl chloride and aminoguanidine, the compounds shown in Table II are obtained and identified by NMR and mass spectral analyses.

TABLE II

| Ex. No. | R1 | R2 | R3 | R6 |
|---|---|---|---|---|
| 8 | H | H | H | 4-biphenyl |
| 9 | H | H | H | 4-bromophenyl |
| 10 | H | H | H | 5-chloro-2-methoxyphenyl |
| 11 | —CH₂—CH₂—CH₂— | | H | phenyl |
| 12 | —CH₂—CH₂— | | CH₃ | phenyl |

EXAMPLE 13

Preparation of 2-{(E)-1-[2,4-Dimethyl-1-(phenylsulfonyl)-1H-pyrrol-3-yl]ethylidine} hydrazinecarboximidamide Hydrochloride

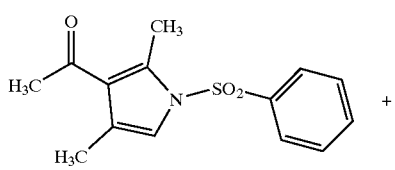

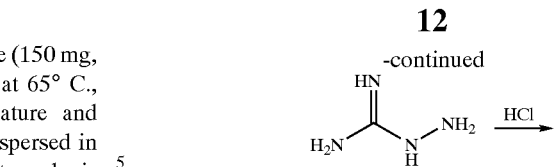

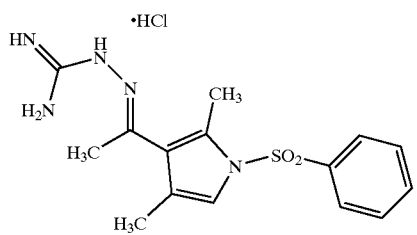

A stirred solution of 1-[2,4-dimethyl-1-phenylsulfonyl)-1H-pyrrol-3-yl]-1-ethanone (277 mg, 1 mmol) in isopropanol is treated with aminoguanidine bicarbonate (150 mg, 1.1 mol) and concentrated HCl (1 ml), heated at 60° C. under $N_2$ for 18 hr, cooled to room temperature and concentrated in vacuo. The resultant residue is dispersed in methylene chloride and water and filtered. The filter cake is air-dried to give the title product as an off-white solid, 225 mg (69% yield) mp 256–258° C., identified by NMR and mass spectral analyses.

EXAMPLES 14–21

Preparation of 2-1-Arylsulfonyl-1H-pyrrol-3-yl-ethylidene Hydrazinecarboximidamide Hydrochloride

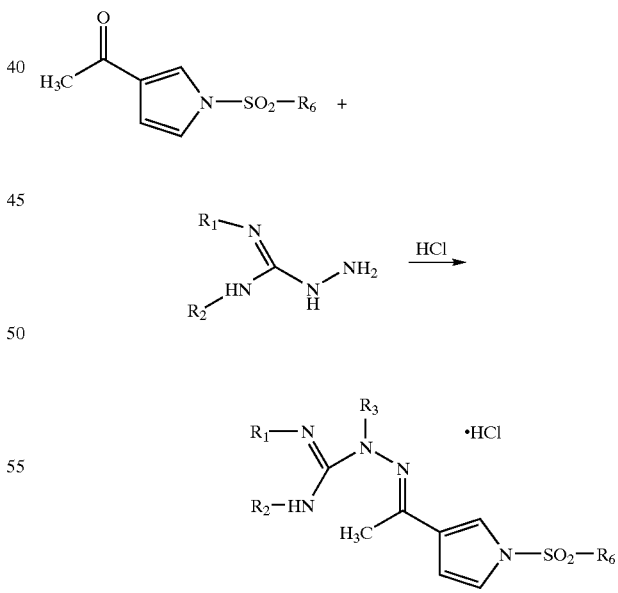

Using essentially the same procedure described in Example 13 and substituting the appropriate 1-arylsulfonyl-3-acetylpyrrole and aminoguanidine derivative, the compounds shown in Table III are obtained and identified by NMR and mass spectral analyses.

Table III

[Structure: R1-N=C(NH-R2)-N(R3)-N=C(CH3)-pyrrole-N-SO2-R6 · HCl]

| Ex. No. | R1 | R2 | R3 | R6 | mp °C. | % Yield |
|---|---|---|---|---|---|---|
| 14 | H | H | H | phenyl | 220–221 | 71 |
| 15 | H | H | H | 4-methylphenyl | 277–279 | 81 |
| 16 | H | H | H | 1-naphthyl | 280 (dec) | 93 |
| 17 | H | H | H | 5-chloro-3-methyl-1-benzothiophen-2-yl | 285 (dec) | 90 |
| 18 | H | H | H | 4-aminophenyl | 198–200 | 92 |
| 19 | H | H | H | 2-amino-4-methyl-1,3-thiazol-5-yl | 225 (dec) | 81 |
| 20 | —CH$_2$CH$_2$—CH$_2$— | | H | phenyl | — | — |
| 21 | —CH$_2$—CH$_2$— | | CH$_3$ | phenyl | — | — |

EXAMPLE 22
Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 $\mu$l volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 $\mu$l. To each well is added the following mixture: 80.0 $\mu$l of incubation buffer made in 50 mM Tris.HCl buffer (pH 7.4) containing 10.0 mM MgCl$_2$ and 0.5 mM EDTA and 20 $\mu$l of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 $\mu$l of tissue suspension. Nonspecific binding is measured in the presence of 10.0 $\mu$M methiothepin. The test compounds are added in 20.0 $\mu$l volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 $\mu$l Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 $\mu$M unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points is plotted, from which the IC$_{50}$ value is determined and the K$_i$ value is determined based upon the following equation:

$$K_i = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table IV, below.

TABLE IV

| Test Compound (Ex. No.) | 5-HT6 Binding Ki (nM) |
|---|---|
| 7 | 37.0 |
| 13 | 6.0 |
| 14 | 1.5 |
| 15 | 5.5 |
| 16 | 2.0 |
| 17 | 32.0 |
| 18 | 0.6 |
| 19 | 3.75 |

TABLE IV-continued

| Test Compound | 5-HT6 Binding Ki (nM) |
| --- | --- |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the present invention demonstrate significant affinity for the 5-HT6 receptor.

What is claimed is:

1. A compound of formula I

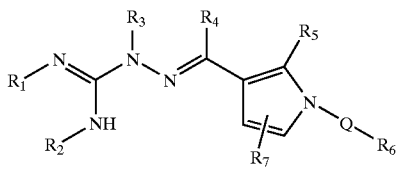

(I)

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a 5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S; or the stereoisomers thereof or the pharmaceutically acceptable salts thereof.

2. The compound according to claim 1 wherein Q is $SO_2$.

3. The compound according to claim 1 wherein $R_5$ is H.

4. The compound according to claim 2 wherein $R_6$ is an optionally substituted aryl or heteroaryl group.

5. The compound according to 4 wherein $R_4$ is H or $CH_3$ and $R_5$ is H.

6. The compound according to claim 5 wherein $R_6$ is an optionally substituted phenyl or heteroaryl group.

7. The compound according to claim 6 wherein $R_7$ is H.

8. The compound according to claim 7 wherein $R_1$, $R_2$ and $R_3$ are H.

9. The compound according to claim 2 selected from the group consisting of:

2-{(E)-1-[1-(phenylsulfonyl)-1H-pyrrol-3-yl]ethylidene}hydrazinecarboximidamide;

2-{(E)-1-[1-(4-methylphenylsulfonyl)-1H-pyrrol-3-yl]ethylidene}hydrazine-carboximidamide;

2-{(E)-1-[1-(2,4-dimethyl-1-(phenylsulfonyl)-1H-pyrrol-3-yl]ethylidene}hydrazine-carboximidamide;

2-{(E)-1-[1-(naphthylsulfonyl)-1H-pyrrol-3-yl]ethylidene}-1-hydrazine-carboximidamide;

2-{(E)-1-{1-(5-chloro-3-methyl-1-benzothiophen-2-yl)sulfonyl]-1H-pyrrol-3-yl}ethylidene)-1-hydrazinecarboximidamide;

2-((E)-1-{1-[(4-aminophenyl)sulfonyl]-1H-pyrrol-3-yl}ethylidene)-1-hydrazine-carboximidamide;

2-((E)-1-{1-[(2-amino-4-methyl-1,3-thiazol-5-yl)sulfonyl]-1H-pyrrol-3-yl)}ethylidene)-1-hydrazinecarboximidamide;

2-[1-[(phenylsulfonyl)-1,5,6,7-tetrahydro-4H-indol-4-ylidene]-1-hydrazinecarboximidamide;

2-[1-(4-biphenylsulfonyl)-1,5,6,7-tetrahydro-4H-indol-4-ylidene]-1-hydrazinecarboximidamide;

2-[1-(4-bromophenylsulfonyl)-1,5,6,7-tetrahydro-4H-indol-4-ylidene]-1-hydrazinecarboximidamide;

2-[1-(5-chloro-2-methoxyphenylsulfonyl)-1,5,6,7-tetrahydro-4H-indol-4-ylidene]-1-hydrazinecarboximidamide;

the stereoisomers thereof; and the pharmaceutically acceptable salts thereof.

10. A method for the treatment of a disorder of the central nervous system related to or affected by the 5-HT6 receptor wherein said disorder is selected from the group consisting of motor disorder, anxiety disorder, cognitive disorder, schizophrenia, depression, Alzheimer's disease, Parkinson's disease, attention deficit disorder and obsessive compulsive disorder, in a patient in need thereof which comprises providing to said patient a therapeutically effective amount of a compound of formula I

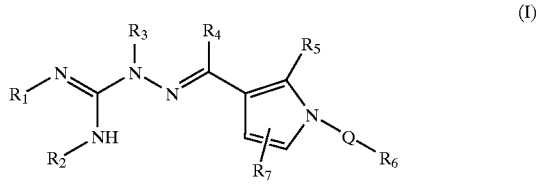

(I)

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a 5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S; or the stereoisomers thereof or the pharmaceutically acceptable salts thereof.

11. The method according to claim 10 wherein said disorder is a motor disorder, anxiety disorder or cognitive disorder.

12. The method according to claim 10 wherein said disorder is schizophrenia or depression.

13. The method according to claim 11 wherein said disorder is selected from the group consisting of: Alzheimer's disease; Parkinson's disease; attention deficit disorder; and obsessive compulsive disorder.

14. The method according to claim 11 having a formula I compound wherein Q is $SO_2$; $R_4$ is H or $CH_3$; $R_5$ is H; and $R_6$ is an optionally substituted phenyl or heteroaryl group.

15. A pharmaceutical composition which comprises a pharmaceutically acceptable carrier and an effective amount of a compound of formula I

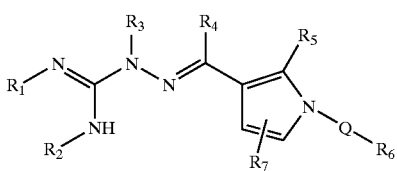

(I)

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a 5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S; or the stereoisomers thereof or the pharmaceutically acceptable salts thereof.

16. The composition according to claim 15 having a formula I compound wherein Q is $SO_2$.

17. The composition according to claim 16 having a formula I wherein $R_4$ is H or $CH_3$ and $R_5$ and $R_7$ are H.

18. The composition according to claim 17 having a formula I compound wherein $R_6$ is an optionally substituted phenyl or heteroaryl group.

19. The composition according to claim 16 having a formula I compound selected from the group consisting of:

2-{(E)-1-[1-(phenylsulfonyl)-1H-pyrrol-3-yl]ethylidene}hydrazinecarboximidamide;

2-{(E)-1-[1-(4-methylphenylsulfonyl)-1H-pyrrol-3-yl]ethylidene}hydrazine-carboximidamide;

2-{(E)-1-[1-(2,4-dimethyl-1-(phenylsulfonyl)-1H-pyrrol-3-yl]ethylidene}hydrazine-carboximidamide;

2-{(E)-1-[1-(naphthylsulfonyl)-1H-pyrrol-3-yl]ethylidene}-1-hydrazine-carboximidamide;

2-{(E)-1-{1-(5-chloro-3-methyl-1-benzothiophen-2-yl)sulfonyl]-1H-pyrrol-3-yl}ethylidene)-1-hydrazinecarboximidamide;

2-((E)-1-{1-[(4-aminophenyl)sulfonyl]-1H-pyrrol-3-yl}ethylidene)-1-hydrazine-carboximidamide;

2-((E)-1-{1-[(2-amino-4-methyl-1,3-thiazol-5-yl)sulfonyl]-1H-pyrrol-3-yl}ethylidene)-1-hydrazinecarboximidamide;

2-[1-[(phenylsulfonyl)-1,5,6,7-tetrahydro-4H-indol-4-ylidene]-1-hydrazinecarboximidamide;

2-[1-(4-biphenylsulfonyl)-1,5,6,7-tetrahydro-4H-indol-4-ylidene]-1-hydrazinecarboximidamide;

2-[1-(4-bromophenylsulfonyl)-1,5,6,7-tetrahydro-4H-indol-4-ylidene]-1-hydrazinecarboximidamide;

2-[1-(5-chloro-2-methoxyphenylsulfonyl)-1,5,6,7-tetrahydro-4H-indol-4-ylidene]-1-hydrazinecarboximidamide;

the stereoisomers thereof; and the pharmaceutically acceptable salts thereof.

20. A process for the preparation of a compound of formula I

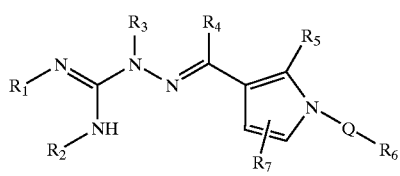

(I)

wherein

Q is $SO_2$, CO, $CH_2$, $CO_2$, CONH or CSNH;

$R_1$, $R_2$, $R_3$ and $R_4$ are each independently H or a $C_1$–$C_6$alkyl, $C_2$–$C_6$alkenyl, $C_2$–$C_6$alkynyl, $C_3$–$C_{10}$cycloalkyl, cycloheteroalkyl, aryl or heteroaryl group each optionally substituted or $R_1$ and $R_2$ may be taken together with the atoms to which they are attached to form a-5-, 6- or 7-membered ring;

$R_5$ is H or $R_4$ and $R_5$ may be taken together with the atoms to which they are attached to form a 5-, 6- or 7-membered ring;

$R_6$ is a $C_1$–$C_6$alkyl, aryl or heteroaryl group each optionally substituted;

$R_7$ is H, halogen, $NO_2$, CN, $OR_8$, $NR_9R_{10}$, $OCO_2R_{11}$, $OCONR_{12}R_{13}$, $CO_2R_{14}$, $COR_{15}$, $CONR_{16}R_{17}$ or $SO_2NR_{18}R_{19}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_8$, $R_{11}$, $R_{14}$ and $R_{15}$ are each independently H or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted; and $R_9$, $R_{10}$, $R_{12}$, $R_{13}$, $R_{16}$, $R_{17}$, $R_{18}$ and $R_{19}$ are each independently H or an optionally substituted $C_1$–$C_6$alkyl group or $R_9$ and $R_{10}$ may be taken together with the atom to which they are attached to form a 5-, 6- or 7-membered ring optionally containing another heteroatom selected from O, N or S which process comprises reacting a compound of formula (IIa)

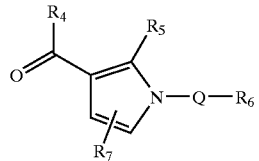

wherein Q, $R_4$, $R_5$, $R_6$ and $R_7$ are as described hereinabove with an aminoguanidine of formula IV (IV)

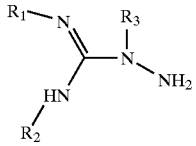

wherein $R_1$, $R_2$ and $R_3$ are described hereinabove in the presence of an acid optionally in the presence of a solvent.

* * * * *